(12) United States Patent
Broemse et al.

(10) Patent No.: US 10,431,915 B2
(45) Date of Patent: *Oct. 1, 2019

(54) ELECTRONIC SUBASSEMBLY FOR A PERSONAL CARE PRODUCT

(71) Applicant: The Gillette Company LLC, Boston, MA (US)

(72) Inventors: Norbert Broemse, Bad Homburg (DE); Klaus Heubach, Koenigstein (DE); Juergen Behrendt, Niederbrechen (DE)

(73) Assignee: The Gillette Company LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/883,600

(22) Filed: Jan. 30, 2018

(65) Prior Publication Data

US 2018/0159252 A1 Jun. 7, 2018

Related U.S. Application Data

(63) Continuation of application No. 15/377,064, filed on Dec. 13, 2016, now Pat. No. 9,912,087.

(30) Foreign Application Priority Data

Mar. 14, 2016 (EP) ..................................... 16160242

(51) Int. Cl.
| | |
|---|---|
| *H01R 12/00* | (2006.01) |
| *H01R 12/73* | (2011.01) |
| *H01R 13/52* | (2006.01) |
| *H01R 13/516* | (2006.01) |
| *B26B 21/40* | (2006.01) |
| *B26B 21/48* | (2006.01) |
| *A46B 9/04* | (2006.01) |

(Continued)

(52) U.S. Cl.
CPC ............. *H01R 12/732* (2013.01); *A46B 9/04* (2013.01); *A46B 15/0022* (2013.01); *A61C 17/22* (2013.01); *B26B 21/405* (2013.01); *B26B 21/48* (2013.01); *H01R 13/516* (2013.01); *H01R 13/5202* (2013.01); *H01R 13/5213* (2013.01); *H01R 13/5216* (2013.01);
(Continued)

(58) Field of Classification Search
CPC .............. H01R 12/732; H01R 13/5202; H01R 13/5216; H01R 13/5213; H01R 13/516; B26B 21/06; B26B 21/225; B26B 21/48; B26B 21/405; A61C 17/22; A46B 15/0022; A46B 9/04
See application file for complete search history.

(56) References Cited

U.S. PATENT DOCUMENTS

| | | | |
|---|---|---|---|
| 8,984,756 B2 * | 3/2015 | Worrick, III | .......... B26B 21/222 30/50 |
| 9,469,039 B2 | 10/2016 | Hodgson et al. | |

(Continued)

*Primary Examiner* — Jean F Duverne
(74) *Attorney, Agent, or Firm* — John M. Lipchitz

(57) ABSTRACT

An electronic subassembly for a personal care product with a housing defining a chamber. The housing has a tapered guide surface. A first circuit board having a rigid end is positioned within the chamber and a flexible portion positioned outside the chamber. A second circuit board is positioned within the chamber of the housing. The second circuit board has an electrical connector dimensioned to receive the rigid end. An adapter is secured to the first circuit board between the rigid end and the flexible portion. The adapter has a corresponding tapered guide surface that engages the tapered guide surface of the housing to align the rigid end with the electrical connector.

20 Claims, 8 Drawing Sheets

(51) Int. Cl.
  *A46B 15/00* (2006.01)
  *A61C 17/22* (2006.01)
  *B26B 21/06* (2006.01)
  *B26B 21/22* (2006.01)
(52) U.S. Cl.
  CPC ............. *B26B 21/06* (2013.01); *B26B 21/225* (2013.01); *B26B 21/4018* (2013.01)

(56) References Cited

U.S. PATENT DOCUMENTS

| | | |
|---|---|---|
| 9,539,734 B1 | 1/2017 | Bozikis et al. |
| 2014/0310960 A1* | 10/2014 | Ariyanayagam ... B26B 21/4068 30/34.05 |
| 2015/0121703 A1* | 5/2015 | Bridges ............... B26B 21/4018 30/41 |
| 2015/0174775 A1* | 6/2015 | Hodgson ................. B26B 21/30 30/57 |
| 2015/0174776 A1* | 6/2015 | Hawes .................... B26B 21/14 30/526 |
| 2015/0197018 A1* | 7/2015 | Heubach ............... B26B 21/4056 30/34.05 |
| 2015/0197019 A1 | 7/2015 | Hodgson et al. |
| 2015/0321366 A1* | 11/2015 | Papadopoulos-Papageorgis ......... B26B 21/222 30/532 |
| 2015/0328786 A1* | 11/2015 | Shimizu ................ B26B 19/042 30/34.2 |

* cited by examiner

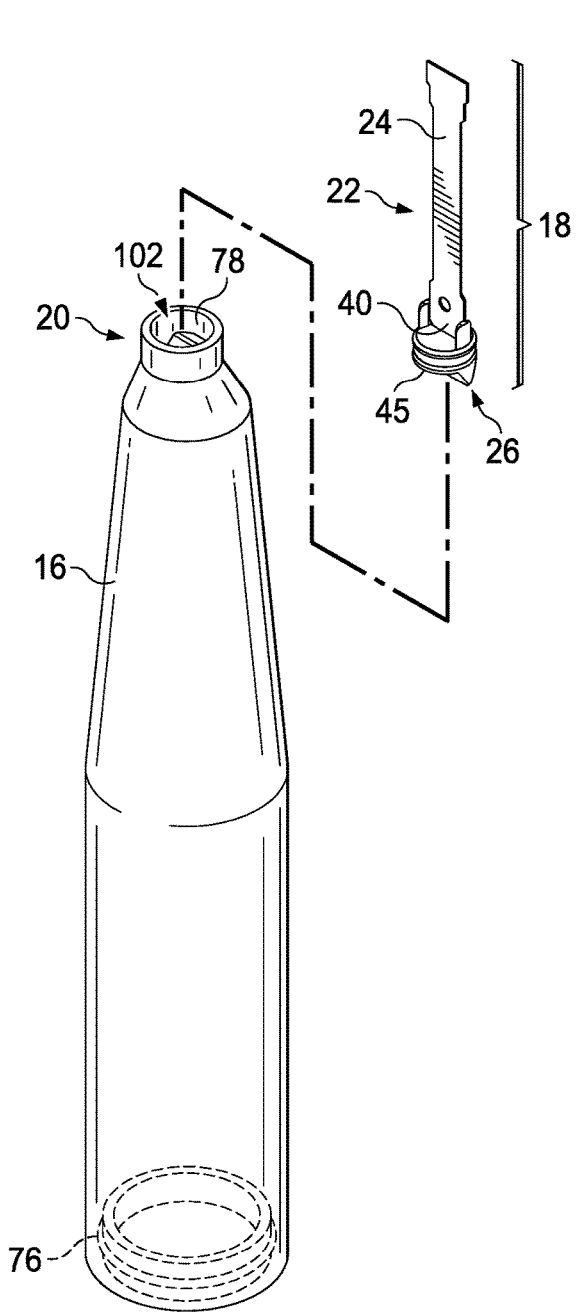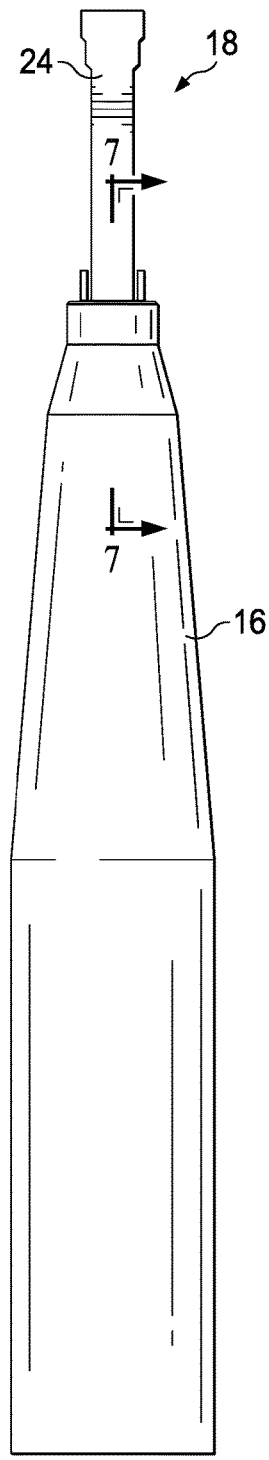
FIG. 5
FIG. 6

ELECTRONIC SUBASSEMBLY FOR A PERSONAL CARE PRODUCT

FIELD OF THE INVENTION

The present invention relates to electronic personal care products and more particularly to heated razors for wet shaving.

BACKGROUND OF THE INVENTION

Personal care products (e.g., consumer appliances) are becoming more advanced and thus often require the incorporation of electronic components to deliver new and/or improved consumer benefits. Electronic components are subject to failure when exposed to a wet environment, such as the bathroom. Furthermore, electronic components must be small to fit within a personal care product, such as a razor or a toothbrush. Accordingly, electrical components and fittings are typically very delicate and can break easily. In order to provide a safe and functional personal care product, the electrical components must be assembled and sealed against water ingress in a reliable cost effective manner.

Accordingly, there is a need to efficiently assemble and seal the electronic components of a personal care product in a simple and reliable manner.

SUMMARY OF THE INVENTION

The invention features, in general, a simple, efficient method of assembling an electronic subassembly for a personal care product by providing an adapter having a body with a tapered guide surface. A first circuit board is positioned within the adapter. A flexible portion of the first circuit board extends from one end of the adapter and a rigid end of the first circuit board extends from the other end of the adapter. A housing is provided with a first opening and a second opening and a chamber between the first and second openings. A second circuit board having an electrical connector into the chamber thru the first opening. The tapered surface of the adapter engages a corresponding tapered guide surface of the housing. The rigid end of the first circuit board is connected to the electrical connector.

The invention also features, in general, a simple, efficient electronic subassembly for a personal care product with a housing defining a chamber. The housing defines a tapered guide surface. A first circuit board having a rigid end is positioned within the chamber and a flexible portion positioned outside the chamber. A second circuit board is positioned within the chamber of the housing. The second circuit board has an electrical connector dimensioned to receive the rigid end. An adapter is secured to the first circuit board between the rigid end and the flexible portion. The adapter has a corresponding tapered guide surface that engages the tapered guide surface of the housing to align the rigid end with the connector.

The details of one or more embodiments of the invention are set forth in the accompanying drawings and the description below. It is understood that certain embodiments may combine elements or components of the invention, which are disclosed in general, but not expressly exemplified or claimed in combination, unless otherwise stated herein. Other features and advantages of the invention will be apparent from the description and drawings, and from the claims.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings.

FIG. 5 is an assembly view of the first and second electronic subassembly.

FIG. 6 is a side view of the first and second electronic subassembly.

DETAILED DESCRIPTION OF THE INVENTION

Figure 1:
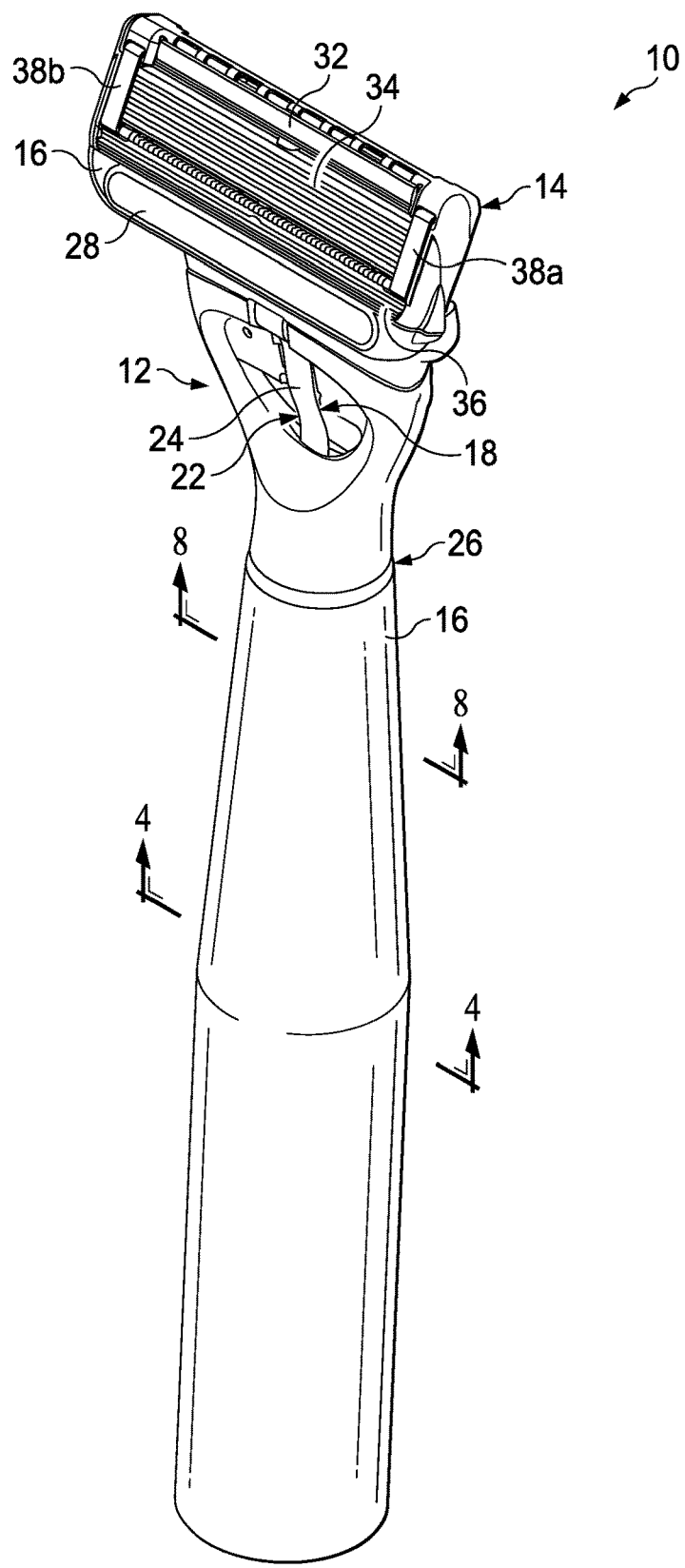
FIG. 1 is a perspective view of one possible embodiment of a personal care product.

Referring to FIG. 1, one possible embodiment of the present disclosure is shown illustrating a personal care product 10 having an electronic subassembly 12. Although the personal care product 10 shown is a wet shaving razor system, it is understood that other personal care products may include, but are not limited to a foil type shaving razor, a toothbrush, a shaving brush, a powered cleansing apparatus, an epilator, and other powered personal care products. These products may be used in a wet environment, such as the bathroom. In certain embodiments, the personal care product 10 may include a cartridge 14 (e.g., a shaving razor cartridge) mounted to a housing 16. The housing 16 may act as a handle for a consumer to hold the personal care product 10. The housing 16 may be injection molded, machined or extruded.

As will be described in further detail below, the electronic subassembly 12 may comprise a first circuit board subassembly 18 and a second circuit board subassembly (not shown) positioned within the housing 16. The first circuit board subassembly 18 may include a first circuit board 22 having a flexible portion 24 and that is mounted to an adapter 26. The adapter 26 may be mounted to the housing 16. At least a portion of the first circuit board 22 may be positioned inside the housing 16 and at least a portion of the first circuit board 22 (e.g., the flexible portion 24) may be positioned outside the housing 16. The adapter 26 may facilitate aligning, coupling and/or securing a portion of the first circuit board 22 within the housing 16. As will be explained in greater detail below, the adapter 26 may be manufactured and secured to the first circuit board 22 as part of an injection molding process or another assembly process. The second circuit board subassembly (not shown) may be completely contained within the housing 16. Various electrical components may be contained within the housing 16 as part of the second circuit board subassembly (not shown). For example, the housing 16 may hold a power source, such as one or more batteries (not shown) that supply power from the second circuit board subassembly (not shown), to the first circuit board subassembly 18 and then to an electrical component 28 located outside the housing 16. In certain embodiments, the electrical component 28 may be a heating element located on a surface of the cartridge 14 or the housing 16 to deliver heat to the skin during shaving. However, the battery in addition to, or alternatively, may supply power to other electrical components including, but not limited to motors, cooling systems and/or lights.

The cartridge 14 may be permanently attached or removably mounted to the housing 16, thus allowing the cartridge 14 to be replaced. The cartridge 14 may have a guard 30, a cap 32 and one or more blades 34 mounted to the cartridge 14 between the cap 32 and the guard 30. The guard 30 may be toward a front portion of the cartridge 14 and the cap 30 may be toward a rear portion of the cartridge 14 (i.e., the guard 30 is in front of the blades 34 and the cap 32 is behind the blades 34). The guard 30 and the cap 32 may define a shaving plane that is tangent to the guard 30 and the cap 32. The guard 30 may be a solid or segmented bar that extends generally parallel to the blades 34.

In certain embodiments, the guard 30 may comprise a skin-engaging member 36 (e.g., a plurality of fins) in front of the blades 34 for stretching the skin during a shaving stroke. The skin-engaging member 36 may be insert injection molded or co-injection molded to the cartridge 14. However, other known assembly methods may also be used such as adhesives, ultrasonic welding, or mechanical fasteners. The skin engaging member 36 may be molded from a softer material (i.e., lower durometer hardness) than the cartridge 14. For example, the skin engaging member 36 may have a Shore A hardness of about 20, 30, or 40 to about 50, 60, or 70. A softer material may enhance skin stretching, as well as provide a more pleasant tactile feel against the skin of the user during shaving. A softer material may also aid in masking the less pleasant feel of the harder material of the cartridge 14 against the skin of the user during shaving.

In certain embodiments, the blades 34 may be mounted to the cartridge 14 and secured by one or more clips 38a and 38b. Other assembly methods known to those skilled in the art may also be used to secure and/or mount the blades 34 to the cartridge 14 including, but not limited to, wire wrapping, cold forming, hot staking, insert molding, ultrasonic welding, and adhesives. The clips 38a and 38b may comprise a metal, such as aluminum for acting as a sacrificial anode to help prevent corrosion of the blades 34. Although five blades 34 are shown, the cartridge 14 may have more or fewer blades depending on the desired performance and cost of the cartridge 14.

In certain embodiments, it may be desirable to provide heat in front of the blades 34. For example, the heating element 28 may be positioned in front of the guard 30 and/or the skin engaging member 36. The heating element 28 may comprise a skin contacting surface (e.g., a face plate) that delivers heat to a consumer's skin during a shaving stroke for an improved shaving experience. However, it is understood the heating element 28 may in addition to or alternatively supply heat to the blades 34, either directly or indirectly. The heating element 28 may be mounted to either the cartridge 14 or to a portion of the housing 16.

Figure 2:
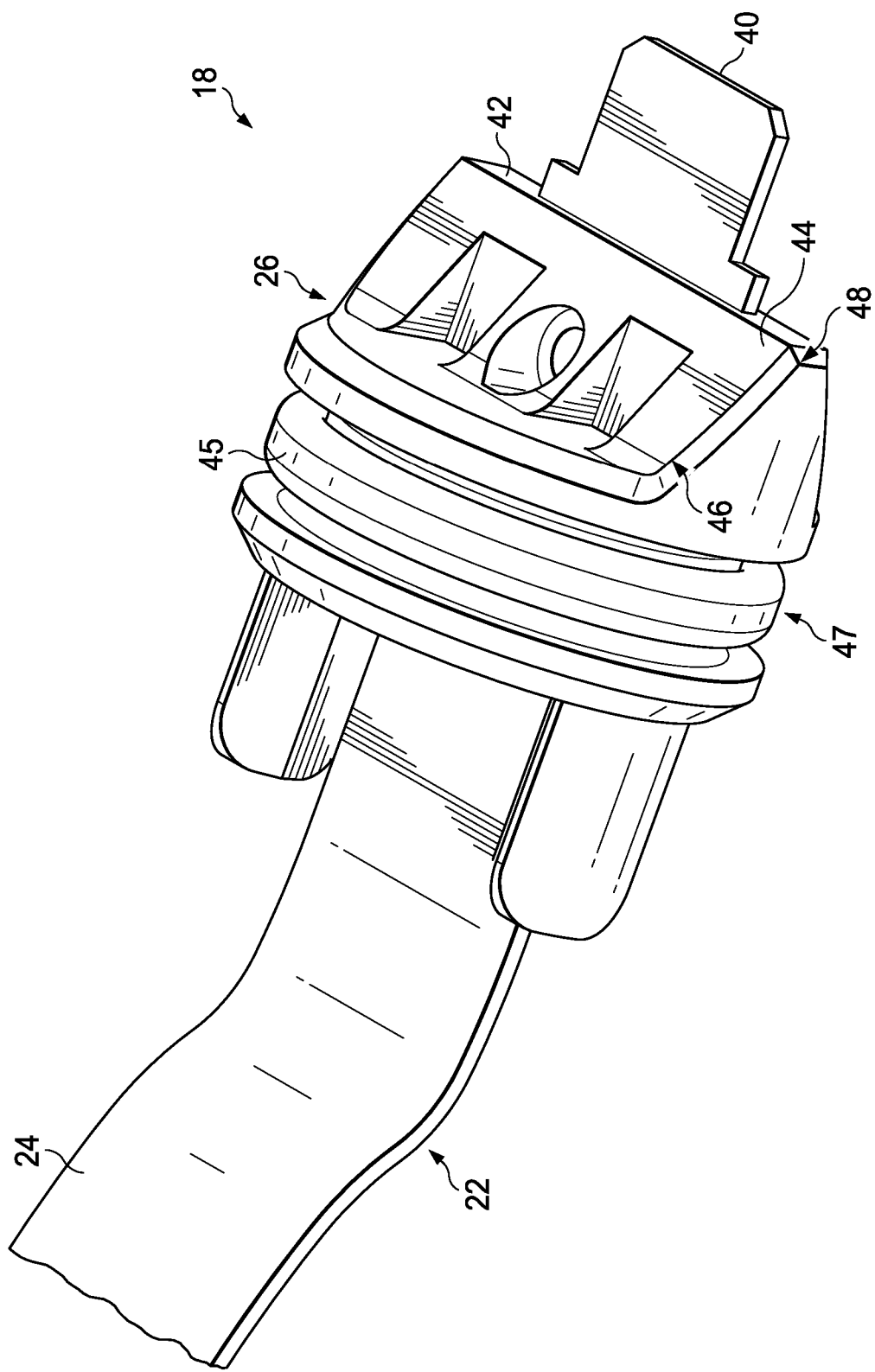
FIG. 2 is a perspective view of one possible embodiment of a first circuit board assembly that may be incorporated into the personal care product of FIG. 1.

Referring to FIG. 2, a perspective view of the first circuit board assembly 18 is shown. The first circuit board assembly may comprise the adapter 26 and the first circuit board 22. The first circuit board 22 may have a rigid end 40 at one end of the flexible portion 24. In certain embodiments, the rigid end 40 may be a separate component that is mounted to the flexible portion 24 to add stiffness and rigidity for improved assembly. The adapter 26 may be secured to the first circuit board 22 between the rigid end 40 and the flexible portion 24. The rigid end 40 may be suspended (e.g., unsupported) and extend from an end 42 of the adapter 26 to facilitate the coupling of the rigid end 40 to the second circuit board (not shown). The rigid end 40 may be sufficiently stiff such that it does not deflect during assembly. If the rigid end 40 deflects, it may be difficult to align and/or connect other electrical components to first circuit board assembly 18. In certain embodiments, the rigid end 40 may have an unsupported length that extends about 2 mm to about 12 mm from the end 42 of the adapter 26 to allow for proper connection to other electrical components.

The adapter 26 and the first circuit board 22 may be interconnected as part of a manufacturing operation (e.g., insert injection molding). A portion of the first circuit board 22 (e.g., part of the rigid end 40) may be placed in an injection and plastic (e.g., that forms the adapter 26) may be injected around a portion (e.g., the rigid end 40) of the first circuit board 22. The adapter 26 may have a tapered guide surface 44 that tapers from a thicker region 46 to a thinner region 48 nearer the end 42. The adapter 26 may have a sealing surface 45 (e.g., on the thicker region 46) to provide a fluid seal after the adapter 26 is assembled to the housing 16. In certain embodiments, the sealing surface 45 may include a sealing member 47, such as an O-ring, between the adapter 26 and the housing. As will be explained in greater detail below, molding of the adapter 26 around a portion of the rigid end 40 may allow not only for sealing the rigid end 40 from water ingress, but may also allow for the precise positioning of the rigid end 40 within the housing 16 (not shown).

Figure 3:
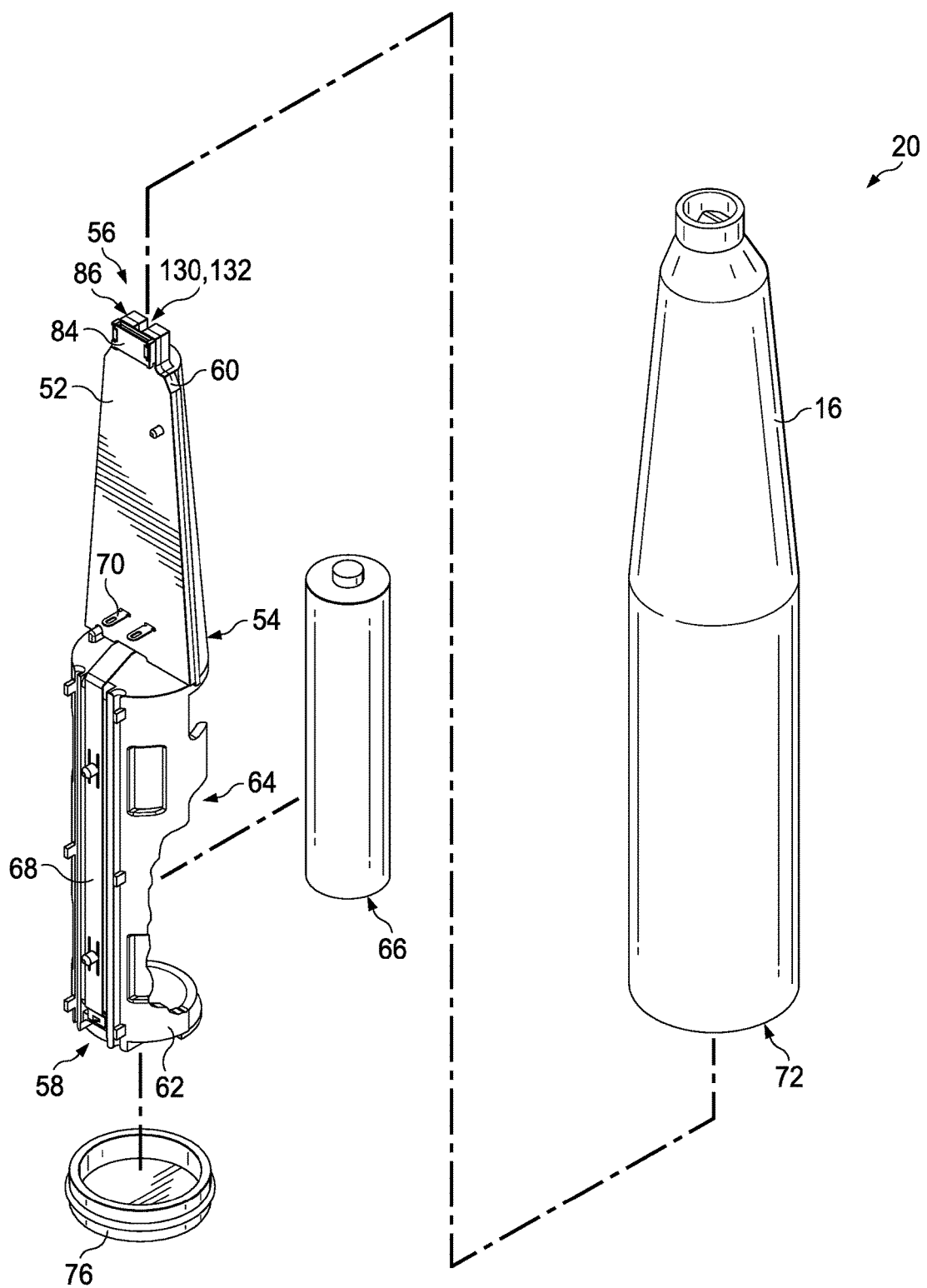
FIG. 3 is an assembly view of one possible embodiment of a second circuit board that may be incorporated into the personal care product of FIG. 1.

Referring to FIG. 3, an assembly view of the second circuit board subassembly 20 is illustrated. The second circuit board subassembly 20 may include a second circuit board 52 supported by a chassis 54, which are positioned within the housing 16. The chassis 54 may have a first end 56 and a second end 58. The first end 56 may include a platform 60 and the second end 58 may include a battery housing 62. The platform 60 may be flat such that the second circuit board 52 can be securely mounted to the chassis 54 (i.e., the platform 60). The battery housing 62 may be generally cylindrical and define an opening 64 dimensioned to receive one or more batteries 66. In certain embodiments, the battery 66 may include a rechargeable battery. One or more electrical connectors 68, 70 may be used to transfer current from the battery 66 to the second circuit board 52. The one or more electrical connectors 68, 70 may include power rails, clips and/or wires. An electrical connector 84 may be mounted on the second circuit board 52 to facilitate connection between the first circuit board 22 (not shown) and the second circuit board. The housing 16 may have an opening 72 at one end and a second opening 102 at an opposing end. The first opening 72 may be configured to receive the adapter 26 and a second opening 102 may be configured to receive the second circuit board 52. The second circuit board subassembly 20 may be inserted into the opening 72 of the housing 16. As will be described in greater detail below, an end notch 130 may extend into the second circuit board 52. An end notch 132 may also extend into the chassis 54 such that the two end notches 130 and 132 are generally aligned (e.g., overlapping). The end notches 130 and 132 may facilitate proper positioning of the second circuit board subassembly 20 within the housing 16. An end cap 76 may then be positioned over the opening 72 to seal the housing 16 from water ingress. The end cap 76 may be secured to the housing 16 with adhesive, ultrasonic welding, press fit or many other known assembly methods.

Figure 4:
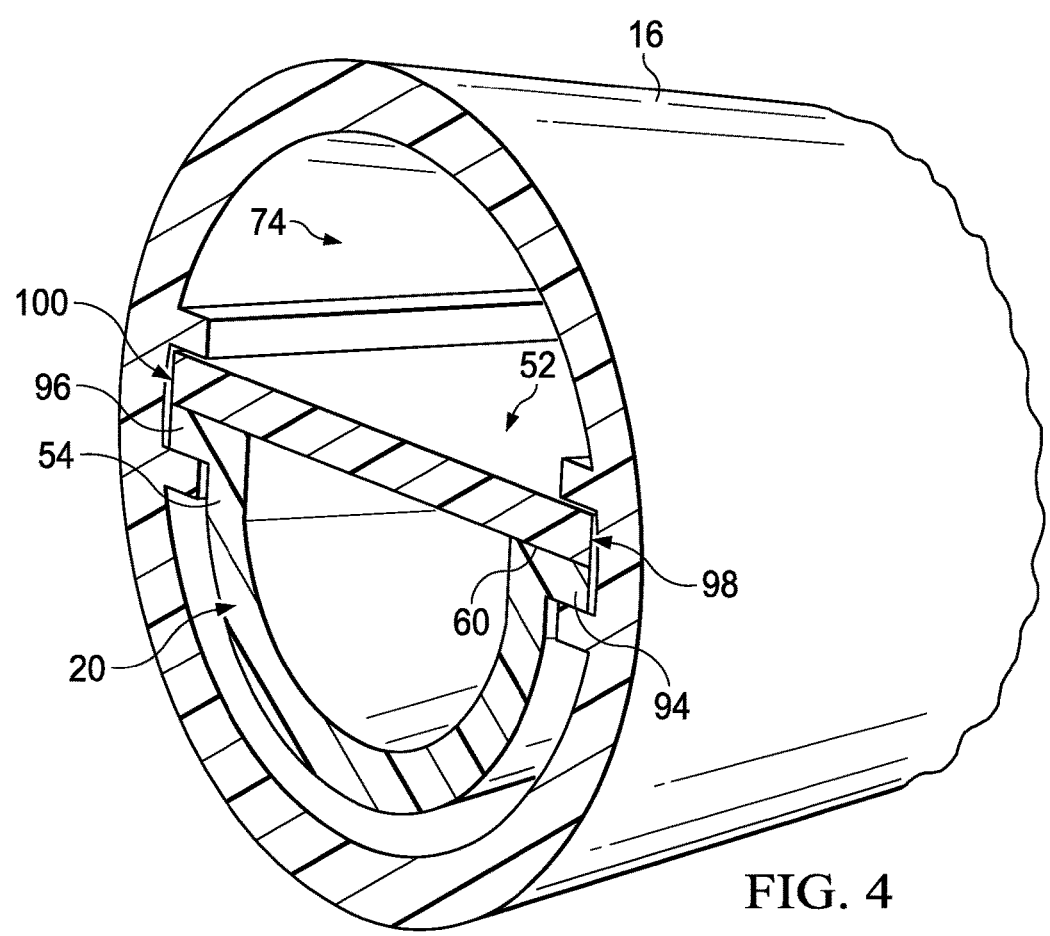
FIG. 4 is a partial cross section view of the personal care product, taken generally along the line 4-4 of FIG. 1.

FIG. 4 is a partial cross section view of the personal care product 10, taken generally along the line 4-4 of FIG. 1. The housing 16 may define a chamber 74 dimensioned to receive the second circuit board subassembly 20. The chamber 74 may be positioned between and in communication with the opening 72 and 102 of the housing (see FIG. 3). The chassis 54 may be dimensioned to allow for easy insertion of the second circuit board subassembly 20 into an opening 72 of the housing 16 (see FIG. 3). The chassis 54 (e.g., the second circuit board 52 and/or the platform 60) may include one or more guide members 94, 96, such as rails and/or grooves to facilitate the precise positioning of the chassis 54, and thus the connector 84 (not shown) within the housing 16. The guide members 94 and 96 may engage a pair of respective guide members 98 and 100, such as channels defined by an inner surface of the housing 16. The channels 98 and 100 may provide sufficient clearance to allow the chassis 54 to easily slide within the housing 16 and guide the connector 84 (see FIG. 3) in a final resting position. The accurate placement of the chassis 54 and the connector 84 facilitates proper alignment and positioning of the chassis 54 within the housing 16. The proper positioning of the chassis 54 (and second circuit board 52) within the housing facilitates the later connection between the rigid end 40 (see FIG. 2) of the first circuit board 22 (see FIG. 2) to the electrical connector 84. Accordingly, guide members 98 and 100 facilitate the self alignment of the second circuit board 52 and the connector 84 (see FIG. 2) within the chamber 74 of the housing 16. As will be explained in greater detail below, the final position of the connector 84 within the housing 16 may also be facilitated by other features of the housing 16 and/or the adapter 26.

Referring to FIG. 5, an assembly view of the first circuit board assembly 18 and the second circuit board assembly 20 is shown. The housing 16 may have an opening 102 dimensioned to receive the adapter 26. In certain embodiments, the second circuit board 52 and the chassis 54 may be positioned within the housing 16 prior to inserting the adapter 26 of the first circuit board assembly 18 into the housing 16. The end cap 76 may also be secured to the housing 16 to help limit movement of the second circuit board 54 within the housing 16 as the adapter 26 is mounted to the housing 16 and provide a fluid seal to prevent water ingress into the housing 16. The adapter 26 may be mounted within the opening 102 of the housing 16 such that the sealing surface 45 of the adapter 26 engages a sealing surface 78 of the housing 16 to provide a fluid seal.

Referring to FIG. 6, a side view of the first circuit board assembly 18 connected to the second circuit board assembly 20 is illustrated. The flexible portion 24 of the first circuit board assembly 18 may extend outside of the housing 16 to allow for attachment to other electrical components.

Figure 7:
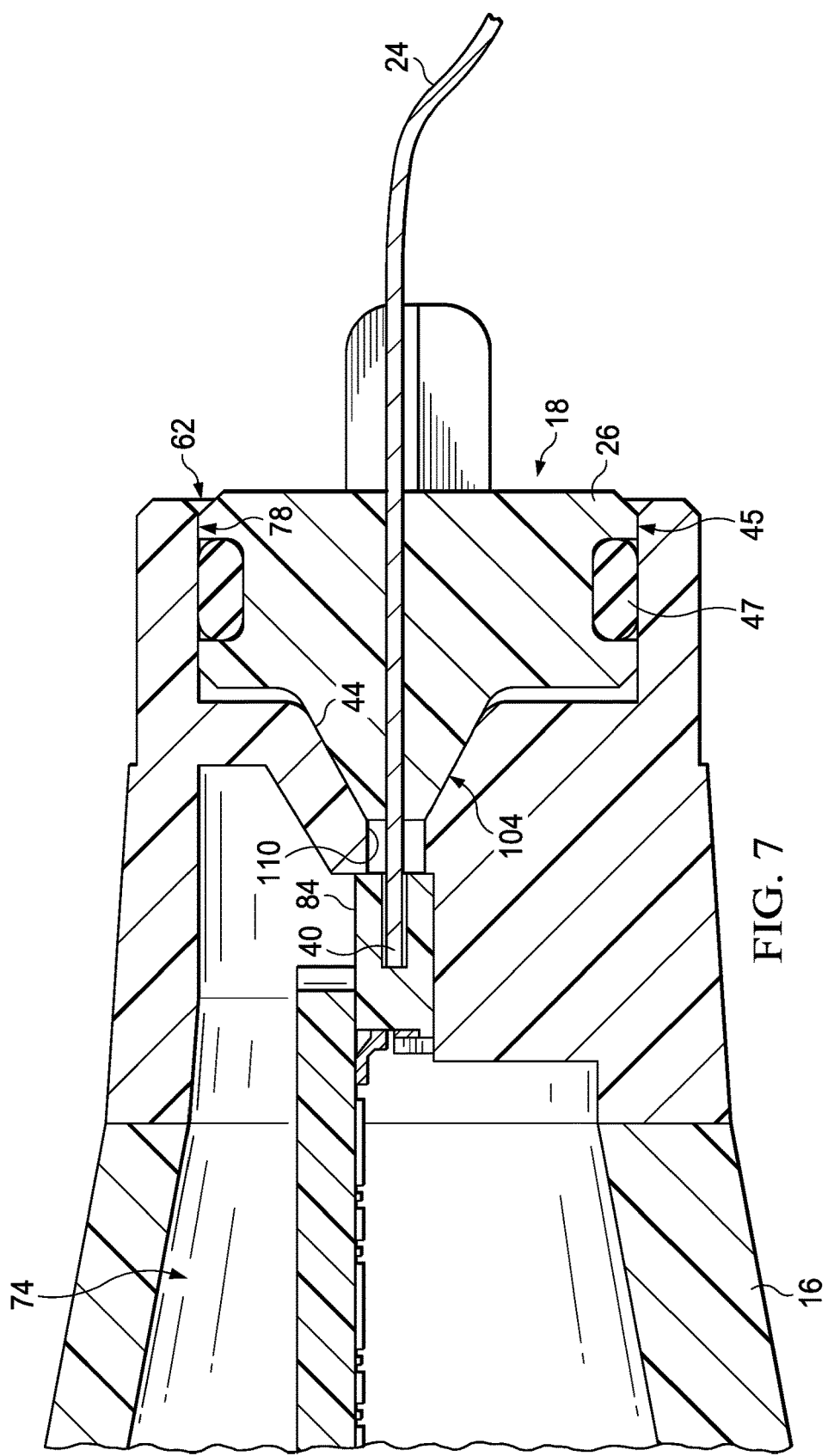
FIG. 7 is a partial cross section view of the first and second electronic subassembly, taken generally along the line 7-7 of FIG. 6.

As shown in FIG. 7, the rigid end 40 may be sealed within the housing 16. FIG. 7 illustrates a cross section view of the electronic sub assembly of FIG. 6 taken generally along the line 7-7 of FIG. 6. As previously described, the second circuit board 52 may be positioned within the chamber 74 of the housing 16 by sliding it in through the second opening 72 (e.g., see FIG. 3) and along the guide members 98 and 100 (e.g., see FIG. 4). The housing 16 and the second circuit board 52 may self align during assembly such that the connector 84 is placed in close proximity with a slot 110 in communication with the opening 102 defined by the housing 16. The adapter 26 is received within the opening 102 of the housing 16. The sealing surface 45 of the adapter 26 engages against the sealing surface 78 of the housing 16 and the sealing member 47 is positioned between the adapter 26 and the housing 16 to help prevent water ingress into the housing 16. The tapered guide surface 44 of the adapter 26 engages the corresponding tapered guide surface 104 of the housing 16 to facilitate the alignment of the rigid end 40 of the first circuit board 22 with the connector 84 of the second circuit board 54. After the adapter 26 is mounted to the housing 16, the rigid end 40 of the first circuit board 22 may be positioned within the housing 16 and the flexible portion 24 of the first circuit board 22 may be positioned outside of the housing 16. Accordingly, the flexible portion 24 may be coupled to other electrical components outside of the housing 16, such as the heating element 28 shown in FIG. 1.

Figure 8:
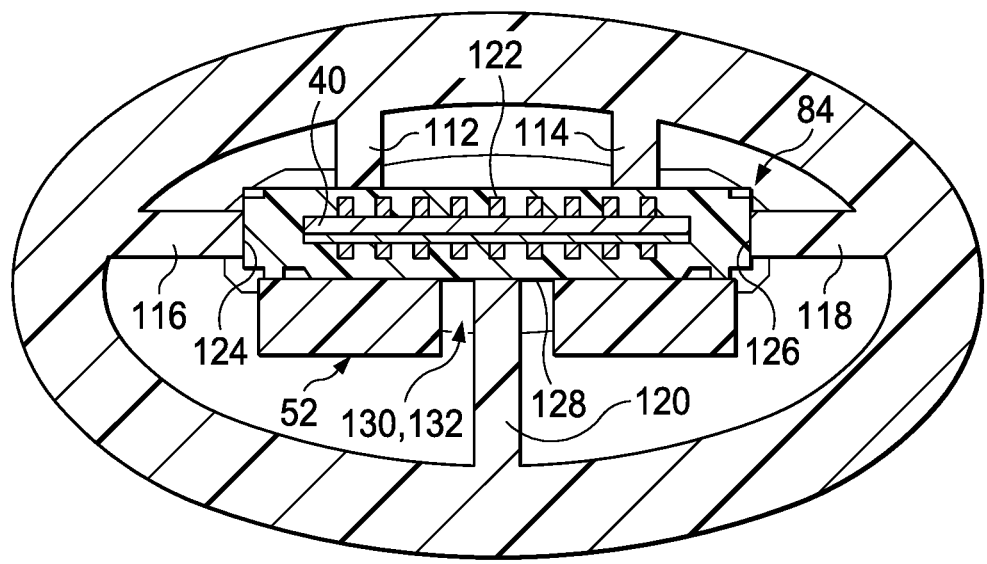
FIG. 8 is a partial cross section assembly view of the personal care product, taken generally along the line 8-8 of FIG. 1.

As shown in FIG. 8, the housing 16 may have a plurality of ribs 112, 114, 116, 118 and 120 that support and guide the final connection of the second circuit board 52 (i.e., the connector 84) to the rigid end 40 of the first circuit board 22. The ribs 112 and 114 may guide a top surface 122 of the connector 84. The ribs 116 and 118 may guide a pair of side surfaces 124, 126 of the connector 84 and the rib 120 may guide a bottom surface 128 of the connector 84. The ribs 112, 114, 116, 118 and 120 facilitate precise alignment of the opening of the connector 84 with the rigid end 40. In certain embodiments, the end notch 130 may extend into the second circuit board 52. The end notch 132 may also extend into the chassis 54 such that the two end notches 130 and 132 are generally aligned (e.g., overlapping). At least one of the end notches 130 and 132 may be dimensioned to receive the alignment rib 120 of the housing. For example, the alignment rib 120 may extend into one or more of the end notches 130, 132 to directly support the electrical connector 84. The engagement of the end notch 130, 132 of the second circuit board 52 with the alignment rib 120 of the housing 16 may facilitate precise positioning of the second circuit board 52 and/or chassis 54 within the housing 16. Furthermore, the alignment rib 120 may provide support to help prevent damage for the second circuit board 52 during assembly or if the housing 16 is dropped.

The ribs 112, 114, 116, 118 and 120 allow a technician to easily place the second circuit board 52 in close proximity to the slot 110 located within the housing (see FIG. 7) without any visual aids (i.e., seeing the final placement of the second circuit board 52 during the assembly process). The technician or assembly machine simply inserts chassis 54 having the second circuit board 52 into the chamber 74 of the housing 16 through the second opening 72 thus putting the connector 84 in the precise position to be able to receive the rigid end 40. Accordingly, the adapter 26 self aligns itself and connects to the electrical connector 84 positioned within the housing 16. In certain embodiments, the second circuit board subassembly 20 may be inserted within the housing 16 prior to inserting the first circuit board assembly 18 into the housing 16. No special fixtures or equipment are needed to aid in the assembly and connection of the first circuit board subassembly 18 to the second circuit board subassembly 20 within the housing 16. The electronic subassembly 12 also eliminates the need to utilize a more complex and costly clam shell type housing, i.e. in two halves, to connect the electronic components because a technician does not need to see the first circuit board and the second circuit board in order to properly connect the two components.

Figure 9:
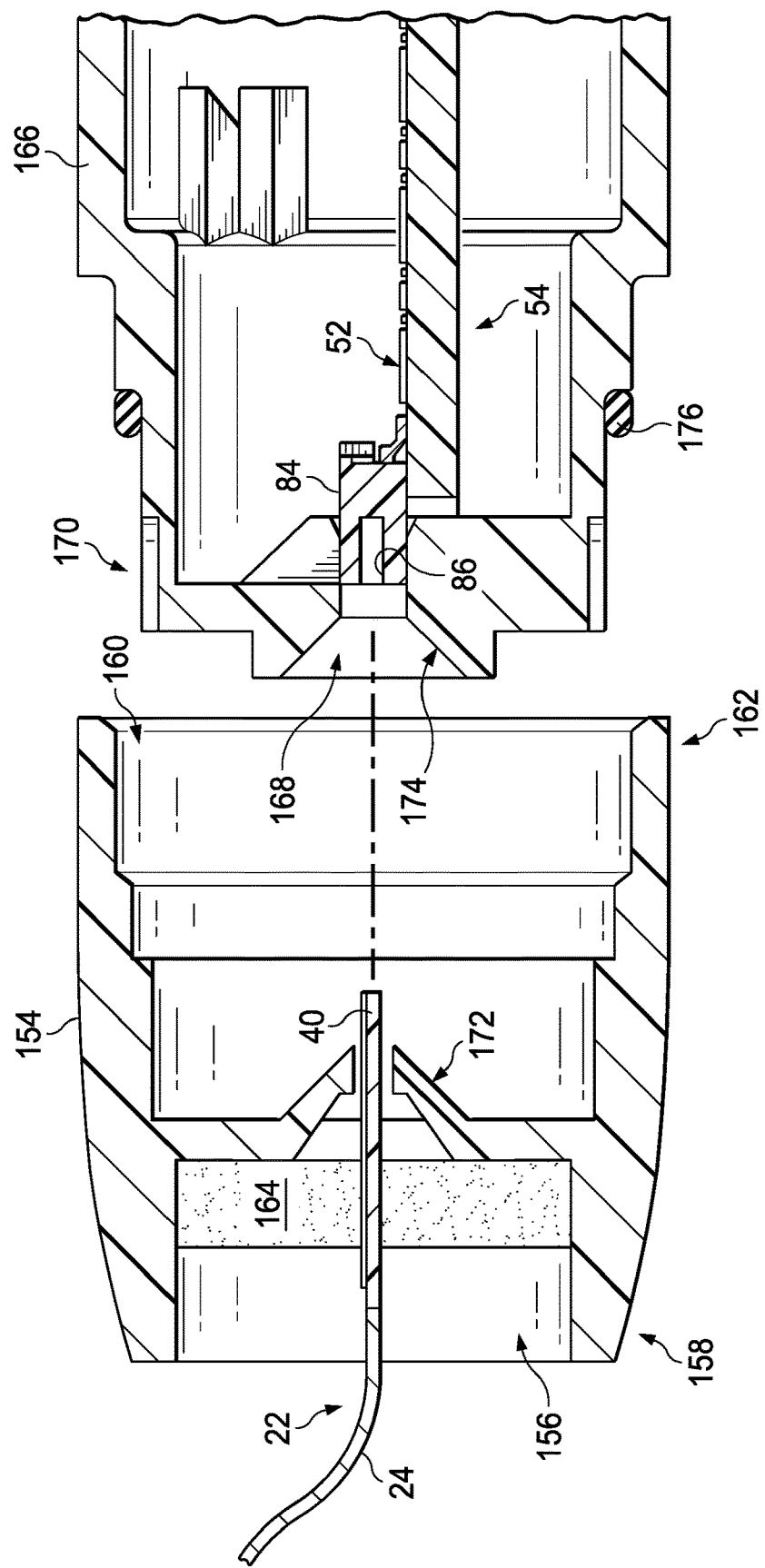
FIG. 9 is a partial cross section view of a second possible embodiment of an electronic subassembly.

Referring to FIG. 9, an alternative embodiment first circuit board assembly 150 is shown being assembled to an alternative embodiment second circuit board assembly 152. The first circuit board assembly 150 may be similar to the first circuit board assembly 18 that has been previously described. For example, the first circuit board assembly 150 may include the first circuit board 22 having the flexible portion 24 and the rigid end 40. However, the first circuit board assembly 150 may have a modified adapter 154 with a recessed surface 156 at one end 158 and a recessed surface 160 at an opposing end 162. The flexible portion 24 may extend out of the recessed surfaced 156 and the rigid end 40 may be positioned within the recessed surface 160 at the opposing end 162. The recessed surface 156 may be filled with a sealant 164 (e.g., a polymeric material) to prevent water ingress into the rigid end 40 and/or the second circuit board assembly 152.

The second circuit board assembly 152 may include a modified housing 166 that contains the second circuit board 54. The housing 166 may have an opening 168 at a first end 170 that is aligned and in communication with the opening 86 of the electrical connector 84. The first end 170 of the second circuit board 54 may be positioned within the end 162 (e.g., recessed surface 160) of the adapter 154. The adapter 154 may have a tapered guide surface 172 that engages a corresponding tapered guide surface 174 on the housing 166. The tapered guide surfaces 172 and 174 may facilitate the assembly of the adapter 154 and the housing 166, as well as, provide for proper alignment of the rigid end 40 and the opening 86 of the connector 84. In certain embodiments, a sealing member 47, such as an O-ring may be positioned between the housing 166 and the adapter 154 to prevent water ingress.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electronic subassembly for a personal care product comprising:
   a housing defining a chamber, the housing defining a tapered guide surface;
   a first circuit board having a rigid end positioned within the chamber and a flexible portion positioned outside the chamber;
   a second circuit board positioned within the chamber of the housing, the second circuit board having an electrical connector dimensioned to receive the rigid end; wherein the tapered guide surface aligns the rigid end with the electrical connector and a sealant filled around the first circuit board preventing water ingress to the rigid end.

2. The electronic subassembly of claim 1 wherein the housing defines a slot in communication with an opening and the electrical connector is in close proximity with the slot.

3. The electronic subassembly of claim 1 wherein the flexible portion is coupled to a heating element.

4. The electronic subassembly of claim 1 wherein the second circuit board is supported by a chassis.

5. The electronic subassembly of claim 4 wherein the chassis has a first end having a platform and a battery housing.

6. The electronic subassembly of claim 5 wherein the second circuit board is mounted on the platform.

7. The electronic subassembly of claim 6 wherein the platform is flat.

8. The electronic subassembly of claim 4 wherein the chassis has a guide member that engages a corresponding guide member on an inner surface of the housing.

9. An electronic subassembly for a personal care product comprising:
   a housing defining a chamber and an opening at a first end of housing in communication with the chamber, the housing defining a tapered guide surface;
   a first circuit board having a rigid end positioned within the chamber and a flexible portion positioned outside the chamber;
   a second circuit board positioned within the chamber of the housing, the second circuit board having an electrical connector dimensioned to receive the rigid end; wherein the electrical connector is in close proximity to a slot in communication with the opening.

10. The electronic subassembly of claim 9 wherein the housing comprises a tapered guide surface aligning the rigid end with the electrical connector.

11. The electronic subassembly of claim 10 further comprising a sealant filled around the first circuit board preventing water ingress to the rigid end.

12. The electronic subassembly of claim 9 wherein the flexible portion is coupled to a heating element.

13. The electronic subassembly of claim 9 wherein the second circuit board is supported by a chassis.

14. The electronic subassembly of claim 13 wherein the chassis has a first end having a platform and a battery housing.

15. The electronic subassembly of claim 14 wherein the second circuit board is mounted on the platform.

16. The electronic subassembly of claim 15 wherein the platform is flat.

17. The electronic subassembly of claim 15 wherein the chassis has a guide member that engages a corresponding guide member on an inner surface of the housing.

18. An electronic subassembly for a personal care product comprising:
   a housing defining a chamber in communication with an opening at a first end of the housing;
   a first circuit board having a rigid end positioned within the chamber and a flexible portion positioned outside the chamber;
   a sealant filled around the first circuit board preventing water ingress to the rigid end;
   a second circuit board positioned within the chamber of the housing, the second circuit board having an electrical connector dimensioned to receive the rigid end and in close proximity to a slot in communication with the opening, wherein the housing has a tapered guide surface aligning the rigid end with the electrical connector.

19. The electronic subassembly of claim 18 wherein the flexible portion is coupled to a heating element.

20. The electronic subassembly of claim 18 wherein the second circuit board is supported by a chassis having a first end with a platform and second end having a battery housing.

* * * * *